United States Patent
Colaiocco et al.

(10) Patent No.: US 6,477,516 B1
(45) Date of Patent: Nov. 5, 2002

(54) SYSTEM AND METHOD FOR PREDICTING PARAMETER OF HYDROCARBON WITH SPECTROSCOPY AND NEURAL NETWORKS

(75) Inventors: Silvia Rosa Colaiocco, Miranda; Youssef Euclio Espidel, La Victoria, both of (VE)

(73) Assignee: Intevep, S.A., Caracas (VE)

( * ) Notice: Subject to any disclaimer, the term of this patent is extended or adjusted under 35 U.S.C. 154(b) by 0 days.

(21) Appl. No.: 09/571,232

(22) Filed: May 16, 2000

(51) Int. Cl.$^7$ .............................................. G06F 15/18
(52) U.S. Cl. ......................................... 706/21; 324/303
(58) Field of Search ................................ 324/306, 307, 324/303; 706/21

(56) References Cited

U.S. PATENT DOCUMENTS

| | | | | |
|---|---|---|---|---|
| 5,218,529 A | * | 6/1993 | Meyer et al. .................. | 702/28 |
| 5,302,897 A | * | 4/1994 | Tache et al. ................. | 324/307 |
| 5,319,308 A | * | 6/1994 | Dechene et al. ............. | 324/307 |
| 5,519,319 A | * | 5/1996 | Smith et al. ................. | 324/306 |
| 5,530,350 A | * | 6/1996 | Dechene et al. ............. | 324/306 |
| 5,625,750 A | * | 4/1997 | Puskorius et al. ............ | 706/21 |
| 5,650,722 A | * | 7/1997 | Smith et al. ................. | 324/307 |
| 5,675,253 A | * | 10/1997 | Smith et al. ................. | 324/306 |
| 5,871,805 A | * | 2/1999 | Lemeison ..................... | 427/8 |
| 6,060,293 A | * | 5/2000 | Bohr et al. ............... | 435/173.1 |
| 6,255,819 B1 | * | 7/2001 | Day et al. .................... | 324/303 |
| 6,272,479 B1 | * | 8/2001 | Furry et al. ................... | 706/13 |
| 6,295,504 B1 | * | 9/2001 | Ye et al. ........................ | 702/7 |
| 6,337,568 B1 | * | 1/2002 | Tutunji et al. ............... | 324/303 |
| 6,341,629 B1 | * | 1/2002 | Clark et al. ................... | 141/83 |

FOREIGN PATENT DOCUMENTS

| | | | | |
|---|---|---|---|---|
| WO | WO9202886 | 2/1992 | | |
| WO | WO 92/02886 | * | 2/1992 | ........... G06F/15/18 |

OTHER PUBLICATIONS

Average molecular weight of oil fractions by nuclear magnetic resonance, Viadimir Leon; Fuel 1987, vol. 66 Oct.*

Estimation of average structural parameters of bitumens by 13c nuclear resonance spectroscopy, Laurent Michon; Didier Martin; Jean–Pascal Planche and Bernard Hanquet; Feul (1997) vol. 76, No. 1.*

Average Molecular Weight of Oil Fractions by Nuclear Magnetic Resonance, by Leon, Fuel, 1987, vol. 66, pp. 1445–1446.

Estimation of Average Structural Parameters of Bitumens 13C Nuclear Magnetic Resonance Spectroscopy, by Michon et al., Fuel, vol. 76, No. 1, pp. 9–15, 1997.

* cited by examiner

*Primary Examiner*—Thomas Black
*Assistant Examiner*—Michael B. Holmes
(74) *Attorney, Agent, or Firm*—Bachman & LaPointe, P.C.

(57) ABSTRACT

A method for predicting parameters of hydrocarbons includes the steps of generating an NMR spectrum of a sample of a hydrocarbon having different hydrogen or carbon types related to structures or sample composition; dividing the NMR spectrum into regions corresponding to the different hydrogen or carbon types related to structures or sample composition; evaluating different spectral regions by either (i) determining average molecular parameters, and (ii) quantifying a signal intensity of said at least one region of said different regions, based upon a desired parameter to be predicted so as to provide spectrum extracted quantities; and applying the spectrum extracted quantities to a trained neural network trained to correlate spectrum extracted quantities with hydrocarbon parameters so as to predict the desired parameters from the spectrum extracted quantity. A system is also provided.

23 Claims, 5 Drawing Sheets

SYSTEM AND METHOD FOR PREDICTING PARAMETER OF HYDROCARBON WITH SPECTROSCOPY AND NEURAL NETWORKS

BACKGROUND OF THE INVENTION

The invention relates to a system and method for predicting parameters of a hydrocarbon using spectroscopy and neural networks.

In the oil industry, it is frequently desirable or necessary to accurately determine crude, feed and product quality parameters in order to comply with customer specifications without quality give away. These determinations are also very useful for advanced process control. There are in existence technologies, like Near Infrared and UV-Visible spectroscopy, that can handle measurements in some of the feedstocks and products processed in the industry. However, these techniques lack the capability of analyzing heavy crude oils and heavy products, due to the fact that they are optical spectroscopies. A way to overcome this situation is by means of Nuclear Magnetic Resonance (NMR) Spectroscopy, which has the capability to detect signals from the entire range of hydrocarbons mentioned above, including the heavy hydrocarbon products.

Some examples of useful heavy products having properties that must be known or measured are heavy distillation cuts, such as vacuum gasoil, vacuum residua, asphalts, pitches and the like. Asphalts are classified, based on rheological properties that have a temperature dependency, according to the Strategic Highway Research Program (SHRP) parameters which frequently must be determined by performing conventional, time consuming laboratory analysis including aging, further processing and the like. For alternative analytical methods, only one publication (Michon, L.; Hanquet, B.; Diawara, B.; Martin, D.; Planche, J-P. Asphalt Study by Neuronal networks. Correlation between Chemical and Rheological Properties. Energy & Fuel, 11, 1188–93, 1997) has been found which attempts to correlate bitumen rheological properties and average molecular parameters using $^{13}C$ NMR and neural networks. The quality of the results of Michon et al. does not comply with the precision and low cost needed for a viable commercial application.

Asphalts are typically a blend of various different hydrocarbon ingredients and actual samples of different blends must conventionally be prepared in order for their properties or parameters to be measured. Clearly, the need remains for a faster yet reliable method for determining such parameters.

Further hydrocarbon products include heavy petroleum products such as pitch, vacuum residua and vacuum gasoil, all of which have properties which must be known in order to determine the potential commercial value of these products. However, determining parameters of these products is subject to the same delays and complications in connection with laboratory analysis as with the asphalt scenario outlined above.

It is therefore the primary object of the present invention to provide a system and method for predicting a parameter of a hydrocarbon.

It is a further object of the present invention to provide a system and method which provide a prediction in a relatively short time period, without sacrificing accuracy.

It is still another object of the present invention to provide a system and method which can be used to predict parameters of various blends of hydrocarbons without requiring preparation of samples of each blend.

It is another object of the present invention to provide a system and method that can be used to predict parameters of a wide range of types of hydrocarbons including heavy hydrocarbons and other hydrocarbons as well.

It is still another object of the present invention to provide a system and method which can be used to predict stability and compatibility parameters of various crude, crude blends, hydrocarbons products and hydrocarbon product blends.

Other objects and advantages of the present invention will appear hereinbelow.

SUMMARY OF THE INVENTION

In accordance with the present invention, the foregoing objects and advantages have been readily attained.

According to one embodiment of the invention, a method is provided for predicting parameters of hydrocarbons, which method comprises the steps of generating an NMR spectrum of a sample of a hydrocarbon; determining at least one average molecular parameter from said spectrum so as to provide at least one spectrum extracted quantity, and applying said at least one spectrum extracted quantity to a trained neural network trained to correlate spectrum extracted quantities with hydrocarbon parameters so as to predict said desired parameter from said spectrum extracted quantity.

According to an another embodiment of the invention, a a method is provided for predicting parameters of hydrocarbons, which method comprises the steps of generating an NMR spectrum of a sample of a hydrocarbon having different hydrogen or carbon types; dividing said NMR spectrum into regions corresponding to said different hydrogen or carbon types; selecting at least one of said regions based upon a desired parameter to be predicted; quantifying a signal intensity of said at least one region, so as to provide at least one spectrum extracted quantity; and applying said at least one spectrum extracted quantity to a trained neural network trained to correlate spectrum extracted quantities with hydrocarbon parameters so as to predict said desired parameter from said spectrum extracted quantity.

In further accordance with the invention, a system has been provided for predicting parameters of hydrocarbons, which system comprises means for generating an NMR spectrum from a hydrocarbon sample; a processor member communicated with said means for generating and adapted to provide at least one spectrum extracted quantity; and a trained neural network communicated with said processor member so as to receive said at least one spectrum extracted quantity, said trained neural network being programmed to correlate spectrum extracted quantities with hydrocarbon parameters so as to predict said desired parameter from said spectrum extracted quantity.

BRIEF DESCRIPTION OF THE DRAWINGS

A detailed description of preferred embodiments of the present invention follows, with reference to the attached drawings wherein.

DETAILED DESCRIPTION

Figure 1:
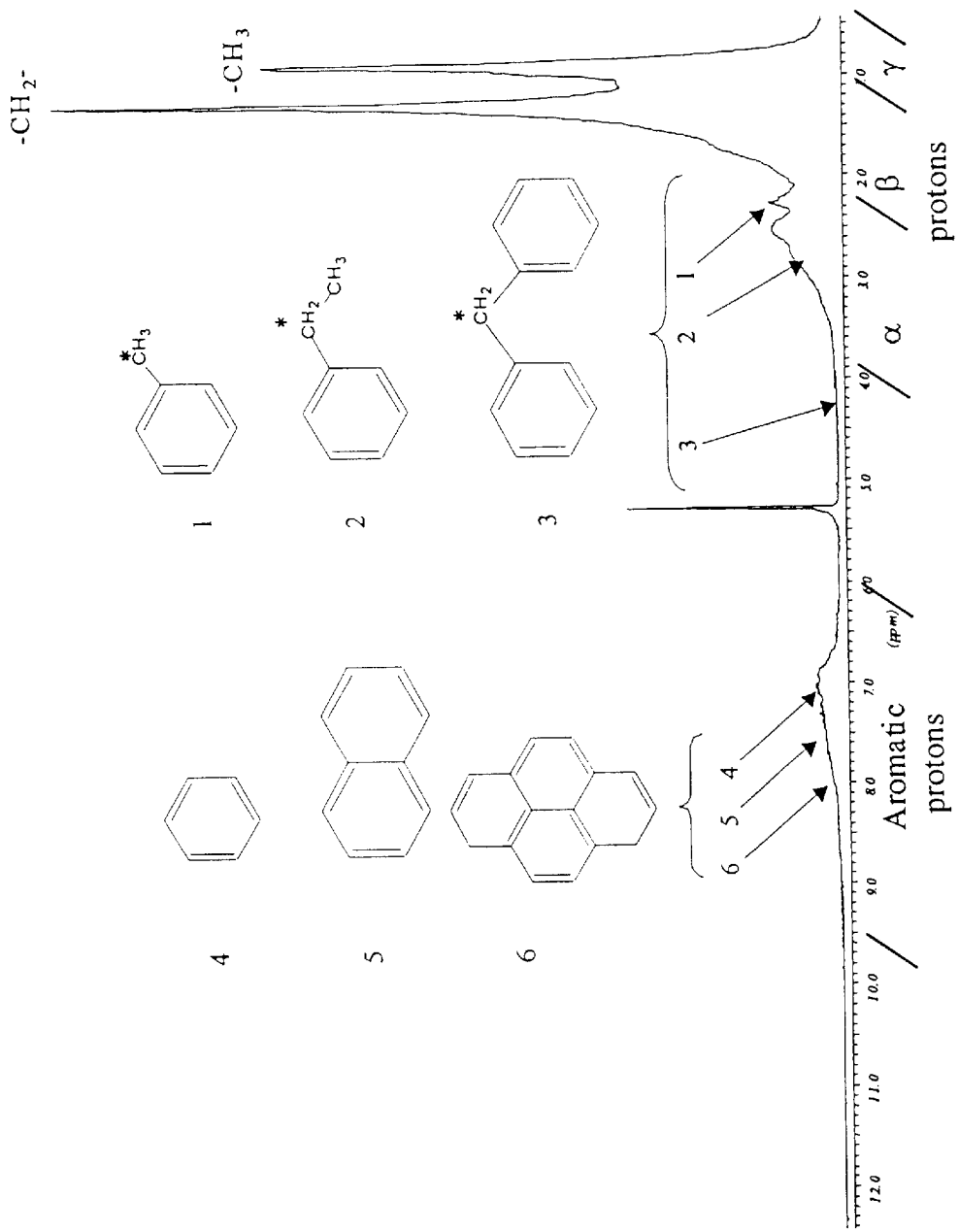
FIG. 1 is a typical $^1H$ or proton NMR spectrum of a hydrocarbon showing different selected regions and their relation to representative molecular structures.

The invention relates to a system and method for predicting parameters of hydrocarbons such as crude oil and light or heavy petroleum products, especially heavy hydrocarbons such as asphalt, coke, pitch, vacuum residua, vacuum gasoil and the like.

Conventionally, hydrocarbon quality parameters such as crude and product quality, crude and product stability or compatibility, product grade, Theological properties, Strategic Highway Research Program (SHRP) parameters and the like must be obtained using time consuming laboratory analysis including in some cases the need for sample aging and the like. In accordance with the present invention, such parameters are predicted using Nuclear Magnetic Resonance (NMR) spectra from which particular information is extracted and then applied to a trained neural network so as to provide a rapid and reliable prediction as to the desired parameter without performing the conventional, time consuming laboratory analysis. The neural network is trained using average molecular parameters or selected spectrum region(s), thereby providing for excellent results in training in the form of shorter prediction times and excellent prediction accuracy.

The invention includes two general facets, or operating modes, namely, training or calibration mode wherein a neural network is trained to include the proper correlation of input and output information, and prediction mode where the system and method are used for determining the desired parameters.

In both training and prediction mode, samples of a particular hydrocarbon are obtained and a NMR spectrum for the sample is generated. This spectrum is obtained using conventional equipment which is well known to the person of ordinary skill in the art. Different types of NMR spectra can be obtained from such samples, including but not limited to $^1H$ or proton NMR spectra and $^{13}C$ NMR spectra. As will be discussed below, the preferred spectrum for use in accordance with the method of the present invention is the $^1H$ NMR spectrum.

The spectrum so obtained is then preferably phased and baseline corrected, and filtered or smoothed so as to provide a spectrum which is then further processed in a spectral feature extraction step so as to obtain or derive a spectrum extracted quantity or quantities which can then be applied to a trained neural network to determine a prediction for the desired parameter.

In accordance with the present invention, the spectral feature extraction step advantageously includes dividing the NMR spectrum into regions which correspond to different hydrogen or carbon types contained in the hydrocarbon of interest, and one or more regions are selected as corresponding to a parameter to be predicted.

The selected region or regions are then further evaluated by one of two alternative embodiments of the present invention, each of which advantageously provides the desired spectrum extracted quantity to be applied to the trained neural network.

In accordance with one embodiment of the present invention, average molecular parameters (AMP) of the hydrocarbon are determined from the selected regions. These average molecular parameters typically include at least one property selected from the group consisting of total number of carbon atoms ($C_t$), saturated carbon atoms weight percentage (% $C_s$), number of alkyl substitutions ($R_s$), carbon atoms per alkyl substitution (N), carbon/hydrogen weight ratio in alkyl substitution (F), number of naphthenic rings per alkyl substitution (R), number of naphthenic rings ($R_n$), number of aromatic carbon atoms ($C_a$), aromatic carbon atoms weight percentage (% $C_a$), aromaticity (fa), number of aromatic rings ($R_a$), number of non-bridge aromatic ring carbon atoms ($C_{anb}$), non-bridge aromatic carbon atoms weight percentage (% $C_{anb}$), substituted aromatic carbon atom weight percentage (% S), and combinations thereof. Of course, other average molecular parameters can be determined and used as a spectrum extracted quantity in accordance with the invention.

One method for determining average molecular parameters from the spectrum is taught in V. León, Average Molecular Weight of Oil Fractions by Nuclear Magnetic Resonance. Fuel, vol. 66, 1445–1446, 1.987. Of course, other methods can be used for determining average molecular parameters from the spectrum or from regions of the spectrum well within the scope of the present invention.

In accordance with this embodiment of the present invention, the average molecular parameter or parameters are used as the spectrum extracted quantity or quantities which can then be applied to a sufficiently trained neural network to obtain the desired parameter prediction. It has been found in accordance with the present invention that average molecular parameters determined from the specific selected regions of the NMR spectrum can provide excellent results in predicting desired parameters for hydrocarbons, advantageously including heavy hydrocarbons.

In accordance with another embodiment of the present invention, the selected region or regions of the NMR spectrum are evaluated by quantifying the signal intensity of the region or regions and using the quantified signal intensity as a spectrum extracted quantity for application to the trained neural network. Quantifying the signal intensity of this region or regions is advantageously accomplished by either measuring the height of the signal in the particular selected region or regions to obtain a quantity or quantities, or by integrating the area of the specific region or regions, also to obtain a particular quantity or quantities. In accordance with the present invention, this embodiment has been found to be particularly advantageous in that accurate predictions can be made as to a wide variety of properties of different hydrocarbons including but not limited to heavy hydrocarbons. This is further preferred when used in connection with the $^1H$ NMR spectrum which, particularly as compared to a $^{13}C$ NMR spectrum, has a high sensitivity nucleus, requires a relatively smaller sample for providing a good spectrum, can be acquired in a period of minutes as opposed to hours for a $^{13}C$ NMR spectrum, and which has a desirably high signal/noise ratio with relatively low integral errors.

FIG. 1 shows an example wherein six specific regions are used in the integration facet of the present invention, for predicting the stability and compatibility values of a crude oil study case. In this example, the spectrum is divided into regions corresponding to aromatic protons, α protons, β protons and γ protons. Of course, other regions could be divided out of the spectrum, if desired, well within the scope of the invention.

The neural network training for the present invention may be performed with the use of any suitable commercial software or system as would be well known to a person of ordinary skill in the art. Although additional layers may be desirable, it has been found that a three layer neural network provides excellent results. The transfer or activation function for each parameter to be modeled using the neural network can be either linear or non-linear, depending on the relationship between inputs and outputs for each layer and independently of the layer.

In training mode, a sample set of a particular type of hydrocarbon is defined, and a suitable number of samples within this set are obtained. NMR spectra are acquired for each sample, and various quality parameters for these samples are determined using standard analytical and/or rheological methods. At the same time, the spectra are pre-processed as discussed above, via phasing, baseline correction, filtering, smoothing and the like, and the spectra are then divided into regions as discussed above which correspond to particular hydrogen or carbon types related to structures or sample composition. For example, specific regions can be identified and separated which correspond to aliphatic and aromatic compositions.

From the separate regions selected, spectra extracted quantities are determined either through determining average molecular parameters, or through quantifying signal intensity, both as discussed above, and this information is combined with the directly measured quality parameters so as to generate a signal extracted quantity/quality parameter matrix which is used as a basis for training the neural network. During the neural network training process the randomized initial weights are adjusted and optimized after each run or epoch (iteration process) until the error is consistently below the acceptable value for the hydrocarbon parameter to be predicted. The neural network is then validated by testing accuracy with various additional known or unknown parameter samples to verify that the outcome is within the acceptable performance standard. Once this level of training has been reached, the neural network model is ready for use and the system and method of the present invention can then be operated in prediction mode as discussed above. It should also be noted that additional external variables may be included in the training mode, such as temperatures, viscosities and the like, so as to provide a system trained to various external conditions as well.

Figure 2:
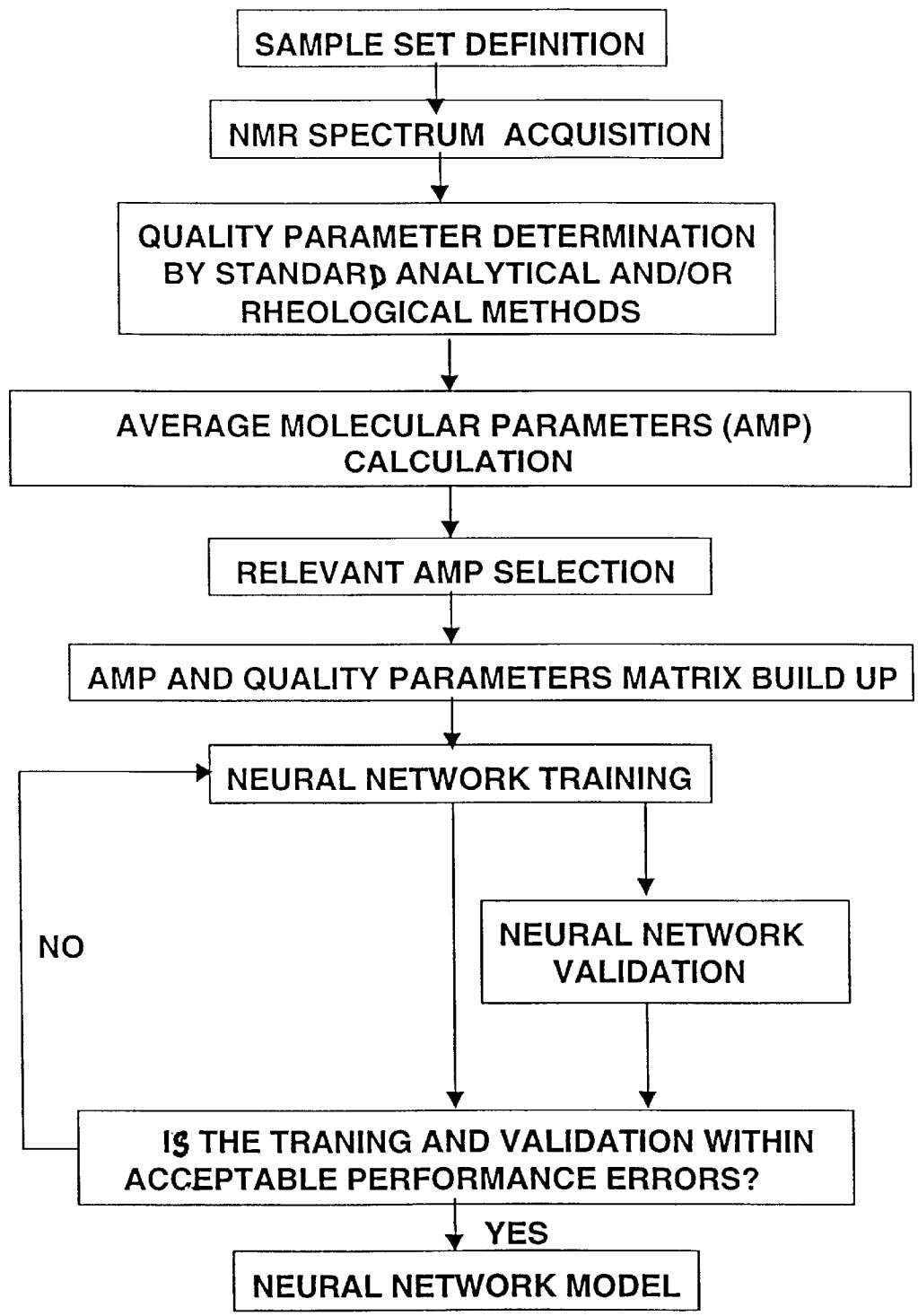
FIG. 2 is a schematic illustration of a calibration procedure for an embodiment of the present invention using average molecule parameters.

Turning now to FIG. 2, one method for training or calibrating a neural network for use in accordance with the method of the present invention is illustrated, specifically in connection with use of average molecular parameters as the signal extracted quantity.

As shown, a sample set is defined, and NMR spectra are acquired from the samples. The quality parameters of the samples of the sample set are determined using standard analytical and/or rheological methods so as to provide output data to be stored in the neural network.

This spectrum is then subjected to spectral feature extraction in accordance with the invention so as to obtain spectrum extracted quantities corresponding to the particular samples, in this case, average molecular parameters of the hydrocarbon. This information is then used to build an AMP/quality parameter matrix which is programmed into the neural network for initial training purposes such that the neural network will accept average molecular parameter inputs and will determine quality parameter outputs from the inputs. The neural network is then validated by testing known samples and comparing predicted results to known results. If the validation is within acceptable performance errors, the neural network is considered trained and ready for use in predicting parameters as desired. If the validation is not within acceptable performance errors, additional training is carried out.

Figure 3:
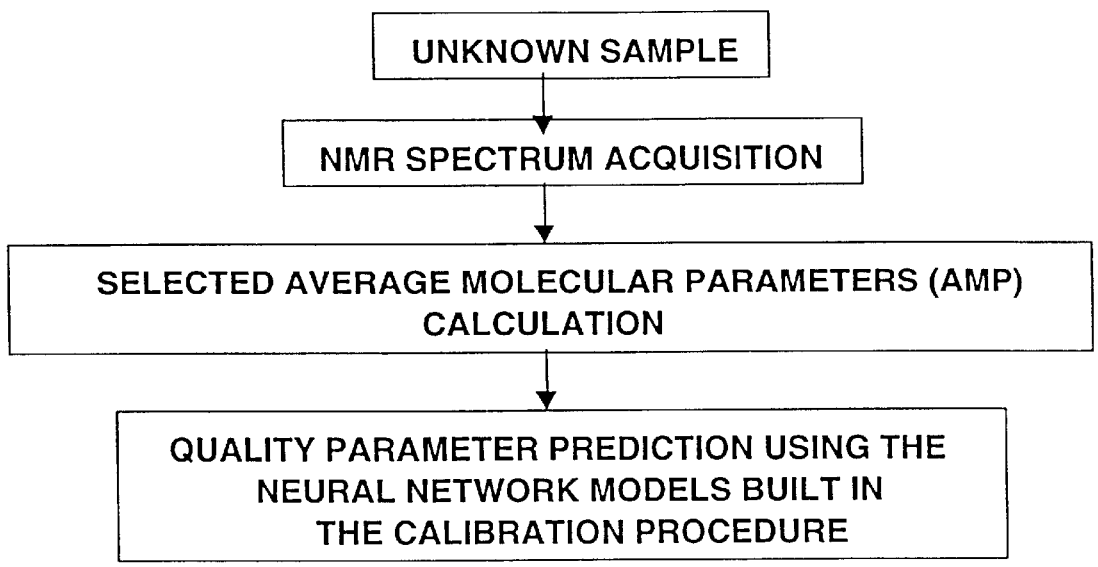
FIG. 3 is a schematic illustration of a prediction procedure for the embodiment of the present invention using average molecule parameters.

FIG. 3 illustrates the operation mode or prediction mode of the method of the present invention in the embodiment which utilizes average molecular parameters. This method is carried out using a trained neural network which has been trained, for example as described in connection with FIG. 2.

Initially, an unknown sample is obtained about which parameters are to be predicted. A NMR spectrum is acquired from this sample, average molecular parameters are calculated using known methods, and these average molecular parameters are then applied to the trained neural network so as to predict the parameter of interest. This prediction, and the training of the neural network in preparation for the prediction, are both carried out by determining average molecular parameters from the NMR spectrum. The method of the present invention advantageously enhances the accuracy of predictions obtained while avoiding the difficulties experienced using conventional lab analysis.

Figure 4:
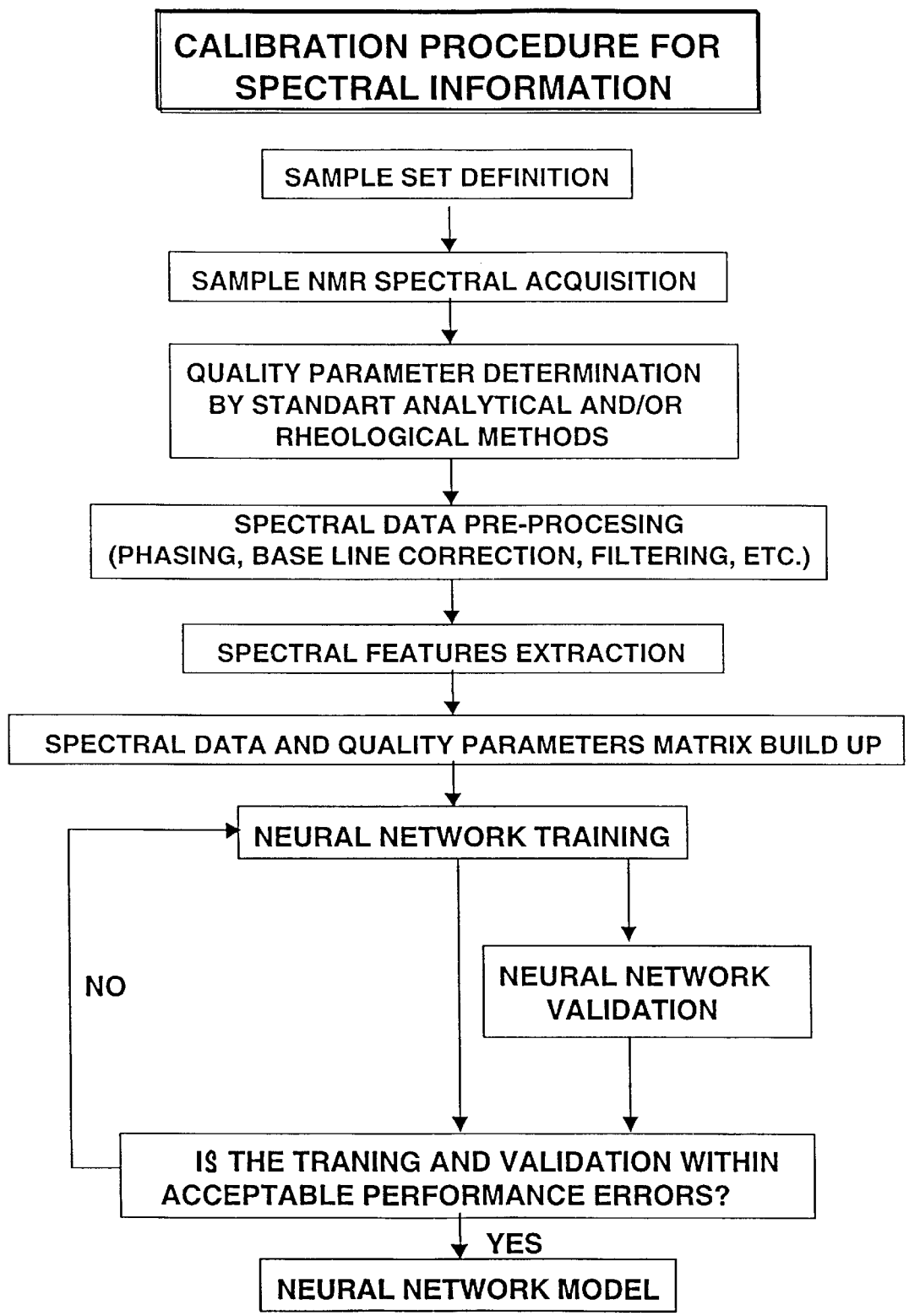
FIG. 4 is a schematic illustration of a calibration procedure for an embodiment of the present invention using signal intensity or integration.
Figure 5:
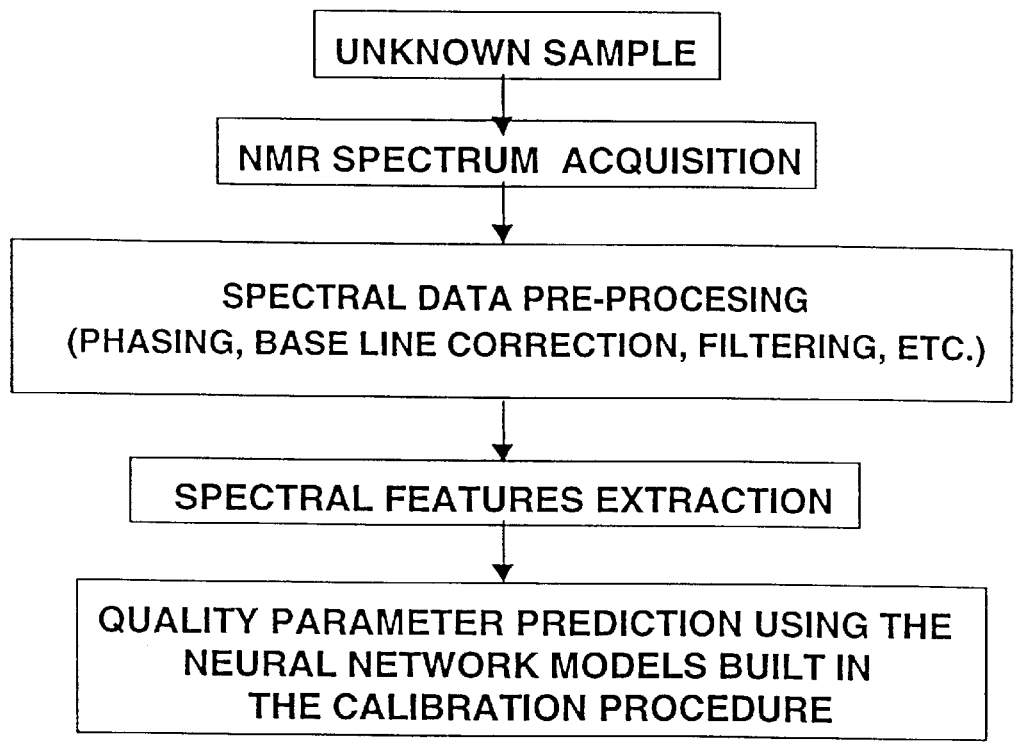
FIG. 5 is a schematic illustration of a prediction procedure for the embodiment of the present invention using signal intensity or integration.

Referring now to FIGS. 4 and 5, training and use methods are described in accordance with the embodiment of the present invention wherein signal intensity of the spectral region or regions are quantified.

FIG. 4 shows the method schematically, wherein a sample set is initially defined and contains a cross-section of samples deemed to be sufficient for the intended use of the neural network to be trained.

As shown, NMR spectra are obtained from these samples, and quality parameters of the hydrocarbons are determined using standard analytical and/or rheological methods so as to provide known parameters for use in training the neural network.

The spectra obtained from the samples are then pre-processed, preferably using phasing, baseline correction, filtering, smoothing and the like so as to provide a pre-process spectrum which is then subjected to spectral feature extraction in accordance with the present invention so as to determine the spectrum extracted quantity as discussed above.

In accordance with this embodiment of the present invention, the spectral feature extraction advantageously includes dividing or separating the spectrum into regions corresponding to the different hydrogen or carbon types related to structures or hydrocarbon composition, for example aliphatic proton type, aromatic proton type and the like or as in FIG. 1, and selection of specific identified regions depending upon the parameters of interest.

The selected region or regions are then further treated, preferably either by integrating the area under the curve or measuring the height of the signal in the particular selected region, so as to obtain a specific quantity used as the spectrum extracted quantity for each region corresponding to that sample. A matrix is then constructed containing the spectrum extracted quantities and analytically determined quality parameters, and this matrix is programmed into a suitable neural network for initial training such that the neural network accepts signal intensity inputs and generates predicted quality parameter outputs based on same.

As with the embodiment of FIG. 2, the neural network is then subjected to validation using further known samples and the validation results are evaluated to determine whether they are acceptable. If the validation provides acceptable results, the neural network is considered trained and is ready for use in prediction. If the errors during validation are unacceptable, the neural network is then subjected to additional training until validation indicates that the neural network model is sufficiently trained. At this point, the trained neural network is ready for use in predicting parameters in accordance with the present invention.

Referring now to FIG. 5, a method for predicting parameters using a trained neural network prepared as illustrated in FIG. 4 is further described.

As shown, a sample of unknown quality is obtained and from this sample is generated an NMR spectrum. The spectrum is pre-processed through phasing and the like as described above, and spectral feature extraction is then performed by dividing the spectrum into regions corresponding to different proton or carbon types, and the same regions used in the training mode are then selected. The selected regions are then quantified either by integration or by measurement of the height of the signal of that region, and this spectrum extracted quantity or combination of quantities is applied to the trained neural network so as to predict the parameter.

In further accordance with the invention, the disclosed system and method can further advantageously be used to predict quality parameters of a combination-product based upon spectra obtained from individual components of the product. For example, a typical asphalt may be prepared using hydrocarbon A and hydrocarbon B, and a different ratio of hydrocarbon A to hydrocarbon B will provide the final asphalt product with different characteristics. In accordance with the present invention, it has been found that parameters can be predicted for such combinations of products without the need for actually preparing samples containing the particular ratios intended.

In accordance with the present invention, this is accomplished by generating an NMR spectrum for each component to be incorporated into a final product. From these spectra, a virtual spectrum can be constructed utilizing the desired ratio of component A to component B, and the virtual spectrum can then be used in accordance with the present invention as disclosed above, utilizing average molecular parameters or signal intensity quantification, to obtain a spectrum extracted quantity for application to a trained neural network to predict the desired parameter. The neural network to be used in this case is trained following the procedures described above, and including a wide enough range of samples so that the virtual spectrum and the quality to be predicted are within the training universe.

In connection with asphalt products, the particular parameters of interest might include SHRP parameters or classifications such as permanent deformation susceptibility (G*/sin θ), permanent deformation susceptibility after RTFOT (G*/sin θ), fragility at low temperature (m and s), fatigue (G*.sin θ) and performance grade (PG grade).

Stability and/or compatibility parameters such as Shell P Value, Heithaus P, $P_o$ and $P_a$ Values and the like can also be determined according to the invention.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A method for predicting a parameter of a hydrocarbon, comprising the steps of:
   generating an NMR spectrum of a sample of a hydrocarbon;
   determining at least one average molecular parameter from said spectrum so as to provide at least one spectrum extracted quantity; and
   applying said at least one spectrum extracted quantity to a trained neural network trained to correlate spectrum extracted quantities with hydrocarbon parameters so as to predict said desired parameter from said spectrum extracted quantity.

2. The method of claim 1, wherein said applying step comprises applying said average molecular parameter to said neural network.

3. The method of claim 1, wherein said generating step comprises generating a $^1$H NMR spectrum of said sample.

4. The method of claim 1, further comprising steps of providing a neural network and training said neural network so as to provide said trained neural network.

5. The method according to claim 4, wherein said training step comprises the steps of:
   (a) obtaining a set of hydrocarbon samples;
   (b) generating NMR spectra for said set of hydrocarbon samples;
   (c) measuring desired quality parameters of said set of hydrocarbon samples so as to provide known quality parameters;
   (d) determining at least one average molecular parameter for said set of NMR spectra for said set of hydrocarbon samples so as to provide at least one spectrum extracted quantity;
   (f) building a matrix of average molecular parameters and quality parameters for said set of hydrocarbon samples; and
   (g) training the neural network with said average molecular parameters and quality parameters matrix to obtain a correlation between average molecular parameters inputs and quality parameters outputs, so as to provide said trained neural network.

6. The method according to claim 1, wherein said sample is a combination of at least two different hydrocarbons, and wherein said generating step comprises generating an NMR spectrum for each hydrocarbon of said at least two different hydrocarbons so as to provide a plurality of separate hydrocarbon spectra, and combining said separate hydrocarbon spectra so as to provide a virtual spectrum for said sample, whereby quality parameters for said sample are predicted without having to make said sample.

7. The method according to claim 1, wherein said hydrocarbon is an asphalt and said hydrocarbon parameter is at least one asphalt SHRP classification selected from the group consisting of permanent deformation susceptibility (G*/sin θ)), permanent deformation susceptibility after RTFOT (G*/sin θ), fragility at low temperature (m and s), fatigue (G*.sin θ) and performance grade (PG grade).

8. The method according to claim 1, wherein said hydrocarbon parameter is at least one value selected from the group consisting of stability values, compatibility values and combinations thereof.

9. The method of claim 8, wherein said values include Shell P values, Heithaus P, $P_o$ and $P_a$ values, and combinations thereof.

10. The method of claim 1, wherein said average molecular properties comprise at least one property selected from the group consisting of total number of carbon atoms ($C_t$), saturated carbon atoms weight percentage (% $C_s$), number of alkyl substitutions ($R_s$), carbon atoms per alkyl substitution (N), carbon/hydrogen weight ratio in alkyl substitution (F), number of naphthenic rings per alkyl substitution (R), number of naphthenic rings ($R_n$), number of aromatic carbon atoms ($C_a$), aromatic carbon atoms weight percentage (% $C_a$), aromaticity (fa), number of aromatic rings ($R_a$), number of non-bridge aromatic ring carbon atoms ($C_{anb}$), non-bridge aromatic carbon atoms weight percentage (% $C_{anb}$), substituted aromatic carbon atom weight percentage (% S), and combinations thereof.

11. A method for predicting parameters of hydrocarbons, comprising the steps of:
   generating an NMR spectrum of a sample of a hydrocarbon having different hydrogen or carbon types;
   dividing said NMR spectrum into regions corresponding to said different hydrogen or carbon types;
   selecting at least one of said regions based upon a desired parameter to be predicted;
   quantifying a signal intensity of said at least one region, so as to provide at least one spectrum extracted quantity; and
   applying said at least one spectrum extracted quantity to a trained neural network trained to correlate spectrum extracted quantities with hydrocarbon parameters so as to predict said desired parameter from said spectrum extracted quantities.

12. The method of claim 11, wherein said quantifying step comprises at least one of integrating area of said at least one region to obtain said signal intensity value, and measuring a signal height of said at least one region to obtain said signal intensity value.

13. The method of claim 11, wherein said generating step comprises generating a $^1$H NMR spectrum of said sample.

14. The method of claim 11, further comprising the steps of providing a neural network and training said neural network so as to provide said trained neural network.

15. The method according to claim 14, wherein said training step comprises the steps of:
   (a) obtaining a set of hydrocarbon samples;
   (b) generating NMR spectra for said set of hydrocarbon samples;
   (c) measuring desired quality parameters of said set of hydrocarbon samples so as to provide known quality parameters;
   (d) dividing said NMR spectra into regions corresponding to different hydrogen or carbon types;
   (e) evaluating said regions by quantifying a signal intensity of said regions, so as to provide a spectrum extracted quantity;
   (f) building a matrix of signal intensity and quality parameters for said set of hydrocarbon samples;
   (g) training said neural network with said matrix of signal intensity and quality parameters to obtain a correlation between signal intensity inputs and quality parameters outputs so as to provide said trained neural network.

16. The method of claim 15, wherein said step of quantifying said signal intensity comprises at least one of integrating area of said at least one region to obtain said signal intensity value, and measuring a signal height of said at least one region to obtain said signal intensity value.

17. The method according to claim 11, wherein said sample is a combination of at least two different hydrocarbons, and wherein said generating step comprises generating an NMR spectrum for each hydrocarbon of said at least two different hydrocarbons so as to provide a plurality of separate hydrocarbon spectra, and combining said separate hydrocarbon spectra so as to provide a virtual spectrum for said sample, whereby quality parameters for said sample are predicted without having to make said sample.

18. The method according to claim 11, wherein said hydrocarbon is an asphalt and said hydrocarbon parameter is at least one asphalt SHRP classification selected from the group consisting of permanent deformation susceptibility (G*/sin θ), permanent deformation susceptibility after RTFOT (G*/sin θ), fragility at low temperature (m and s), fatigue (G*.sin θ) and performance grade (PG grade).

19. The method according to claim 11, wherein said hydrocarbon parameter is at least one value selected from the group consisting of stability values, compatibility values and combinations thereof.

20. The method according to claim 19, wherein said values include Shell P value; Heithaus P, $P_o$ and $P_a$ values, and combinations thereof.

21. A system for predicting a parameter of a hydrocarbon, comprising:
   means for generating an NMR spectrum from a hydrocarbon sample;
   a processor member communicated with said means for generating and adapted to provide at least one spectrum extracted quantity; and
   a trained neural network communicated with said processor member so as to receive said at least one spectrum extracted quantity, said trained neural network being programmed to correlate spectrum extracted quantities with hydrocarbon parameters so as to predict said desired parameter from said spectrum extracted quantity.

22. The system of claim 21, wherein said processor provides said at least one spectrum extracted quantity by at least one of:
   (a) determining average molecular parameters, and
   (b) dividing said spectrum into regions corresponding to different hydrogen or carbon types of said sample; selecting at least one of said regions based upon a desired parameter to be predicted; and evaluating said at least one region by quantifying a signal intensity of said at least one region.

23. The system of claim 21, wherein said processor provides said signal intensity by at least one of integrating area of said at least one region to obtain said signal intensity value, and measuring a signal height of said at least one region to obtain said signal intensity value.

* * * * *